United States Patent
Pei et al.

(10) Patent No.: US 11,578,092 B2
(45) Date of Patent: Feb. 14, 2023

(54) COMPOUND FOR PREVENTING OR TREATING NEURODEGENERATIVE DISEASE AND APPLICATION THEREOF

(71) Applicant: Shanghai Pharmaceuticals Holding Co., Ltd., Shanghai (CN)

(72) Inventors: Gang Pei, Shanghai (CN); Biao Yu, Shanghai (CN); Shichao Huang, Shanghai (CN); Xin Cao, Shanghai (CN); Fuchun Shi, Shanghai (CN); Yue Zhou, Shanghai (CN); Yuqian An, Shanghai (CN); Jing Lu, Shanghai (CN)

(73) Assignee: Shanghai Pharmaceuticals Holding Co., Ltd., Shanghai (CN)

( * ) Notice: Subject to any disclaimer, the term of this patent is extended or adjusted under 35 U.S.C. 154(b) by 132 days.

(21) Appl. No.: 16/967,092

(22) PCT Filed: Jan. 29, 2019

(86) PCT No.: PCT/CN2019/073777
§ 371 (c)(1),
(2) Date: Aug. 3, 2020

(87) PCT Pub. No.: WO2019/154196
PCT Pub. Date: Aug. 15, 2019

(65) Prior Publication Data
US 2021/0040132 A1    Feb. 11, 2021

(30) Foreign Application Priority Data

Feb. 6, 2018 (CN) .......... 201810118796.9

(51) Int. Cl.
*C07H 15/18* (2006.01)
*A61P 25/28* (2006.01)

(52) U.S. Cl.
CPC .............. *C07H 15/18* (2013.01); *A61P 25/28* (2018.01)

(58) Field of Classification Search
CPC ........... C07H 1/00; C07H 13/04; C07H 15/18
See application file for complete search history.

(56) References Cited

U.S. PATENT DOCUMENTS 9,623,063 B2 * 4/2017 Dal Monte ............... A61P 3/10

FOREIGN PATENT DOCUMENTS

| CN | 101914595 A | 12/2010 |
| CN | 106866761 A | 6/2017 |

OTHER PUBLICATIONS

International Search Report dated May 8, 2019 for International Application No. PCT/CN2019/073777.
Zhou et al., "Polyphenols from wolfberry and their bioactivities", Food Chemistry (2016), Jan. 1, 2017, 42 pages, vol. 214, , doi: http://dx.doi.org/10.1016/j.foodchem.2016.07.105.

* cited by examiner

*Primary Examiner* — Pancham Bakshi

(57) ABSTRACT

The present invention relates to a novel compound for preventing or treating neurodegenerative diseases and use thereof. Provided is a novel compound of Formula (I). The compound can effectively promotes the proliferation of neural progenitor cells in both in vitro and in vivo experiments, and can serves as a treatment approach to promote nerve regeneration to fight against cognition impairment associated with aging and neurodegenerative diseases.

11 Claims, 6 Drawing Sheets

COMPOUND FOR PREVENTING OR TREATING NEURODEGENERATIVE DISEASE AND APPLICATION THEREOF

CROSS-REFERENCE TO RELATED APPLICATION

This application is a national stage application, filed under 35 U.S.C. § 371, of International Patent Application No. PCT/CN2019/073777, filed on Jan. 29, 2019, which claims the priority of Chinese application No. 201810118796.9 filed on Feb. 6, 2018, the contents of which are incorporated by reference.

BACKGROUND

Technical Field

The present invention relates to the field of pharmaceutical technology. More specifically, the present invention relates to novel compounds for preventing or treating neurodegenerative diseases and use thereof.

Related Art

Neurodegenerative diseases are a group of diseases caused by chronic progressive degeneration of the central nervous tissue. The diseases mainly include Parkinson's disease (PD), Alzheimer's disease (AD), Huntington's disease (HD), and amyotrophic lateral sclerosis (ALS), etc.

Alzheimer's disease (AD), also known as presenile dementia, is a chronic and progressive neurodegenerative disease, which is mainly manifested by a progressive decline in memory, cognitive dysfunction and loss of independent living and self-care ability. With increasing aging population, the incidence of AD rises year by year, and AD has become the most important public concern of health issues. The main pathological feature of Alzheimer's disease is the formation of amyloid plaques and neurofilament tangles in the brain of the patient. Amyloid plaque is a characteristic pathological change of Alzheimer's disease, which is mainly formed by the extracellular accumulation of amyloid-β (Aβ) protein produced abnormally in a large amount in cells. At present, several theories are proposed to try to explain the pathogenic mechanism. The "Aβ hypothesis" proposed by Hardy and Selkoe is a widely accepted theory. The theory believes that due to the long-term effect of complex genetic and environmental factors, nerve cells abnormally produce Aβ in large amounts, which is accumulated to form oligomers and amyloid plaques. Aβ (especially oligomerized Aβ) undergoes a series of cascade reactions (including such as free radical reaction, mitochondrial oxidative damage and inflammation responses, which directly or indirectly acting on neurons and glial cells), leading to abnormal synaptic function and neuronal damage, and causing the activation of microglia and astrocytes. This accelerates the formation of neurofilament tangles, leading to cognitive impairment after a long time of action. Recently, numerous studies have provided various evidences to support the "Aβ hypothesis", showing the critical role of Aβ in the pathogenesis of Alzheimer's disease.

Parkinson's disease is a common neurodegenerative disease which is clinically manifested by symptoms such as slow response, tremor, body stiffness, and further loss of balance. Studies on brain tissues of PD patients found that the dopaminergic neurons in the substantia nigra of the patients are lost. Lewy inclusion bodies are one of the hallmark lesions of degenerative neurons in Parkinson's disease. Studies have shown that Lewy inclusion bodies are formed in brain tissues of many patients with neurodegenerative diseases, including Alzheimer's disease, Parkinson's disease, and dementia with Lewy body (DLB).

In mammalian brains, the proliferation and self-renewal of neural progenitor cells (NPC) continue throughout the life course and are important parts of neurogenesis. In the case of aging, long-term stress, and neurological diseases such as Alzheimer's Disease (AD), the proliferation and self-renewal ability of neural progenitor cells decreases, leading to impaired cognitive function. Pro-neurogenesis is considered to be a potential treatment against aging and aging-related neurodegenerative diseases. Therefore, a possible solution is cell replacement therapy by transplanting embryonic neural progenitor cells or neural progenitor cells induced in vitro. However, there are still some disputes about this newly created complex technology, especially for the safety and cell sources. Another approach is to activate endogenous neural progenitor cells by pharmacological means to achieve the purpose of treating neurodegenerative diseases. The pharmacological means are easy to operate and can specifically target specific functions of neural progenitor cells. Therefore, activating endogenous neural progenitor cells is not only a feasible treatment, but also a useful prevention method. However, those skilled in the art still need to find suitable drugs that can better penetrate barriers in human body to effectively activate endogenous neural progenitor cells, so as to achieve effective treatment.

SUMMARY

An objective of the present invention is to provide a novel compound for preventing or treating neurodegenerative diseases and use thereof.

In a first aspect, the present invention provides a compound represented by Formula (I) or an isomer, a solvate, a precursor, or a pharmaceutically acceptable salt thereof,

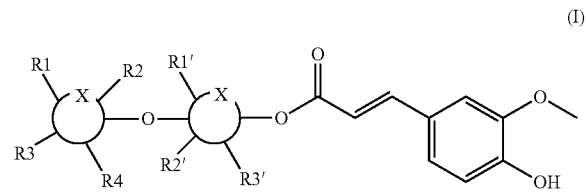

(I)

in which

is a six-membered heterocyclic ring, where X is O; R1-R4 are each independently selected from hydrogen, hydroxyl, C1-C4 alkyl, C2-C4 alkenyl, C2-C4 alkynyl, and halo, or adjacent two groups of R1-R4 are linked to each other to form a cyclic structure with the parent ring; and R1'-R3' are each independently selected from hydrogen, hydroxyl, C1-C4 alkyl, C2-C4 alkenyl, C2-C4 alkynyl, and halo, or adjacent two groups of R1'-R3' are linked to each other to form a cyclic structure with the parent ring.

In a preferred embodiment, in the compound represented by Formula (I) or an isomer, a solvate, a precursor, or a pharmaceutically acceptable salt thereof,

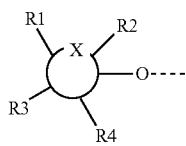

includes a cyclic structure selected from the group consisting of:

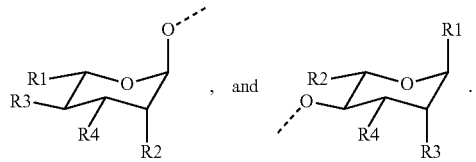

In a preferred embodiment, in the compound represented by Formula (I) or an isomer, a solvate, a precursor, or a pharmaceutically acceptable salt thereof,

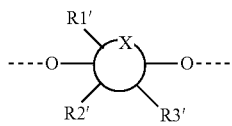

includes the cyclic structure

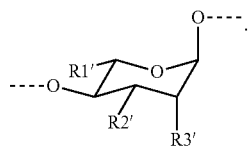

In a preferred embodiment, in the compound represented by Formula (I) or an isomer, a solvate, a precursor, or a pharmaceutically acceptable salt thereof, R1-R4 are each independently selected from hydrogen, hydroxyl, and C1-C2 alkyl, or adjacent two groups of R1-R4 are linked to each other to form a five-membered ring with the parent ring; and R1'-R3' are each independently selected from hydrogen, hydroxyl, and C1-C2 alkyl, or adjacent two groups of R1'-R3' are linked to each other to form a five-membered ring with the parent ring.

In another preferred embodiment, in the compound represented by Formula (I) or an isomer, a solvate, a precursor, or a pharmaceutically acceptable salt thereof, the five-membered ring is an oxygen-containing heterocyclic ring, and preferably, the five-membered ring contains two O atoms.

In another preferred embodiment, the compound represented by Formula (I) or an isomer, a solvate, a precursor, or a pharmaceutically acceptable salt thereof, includes:

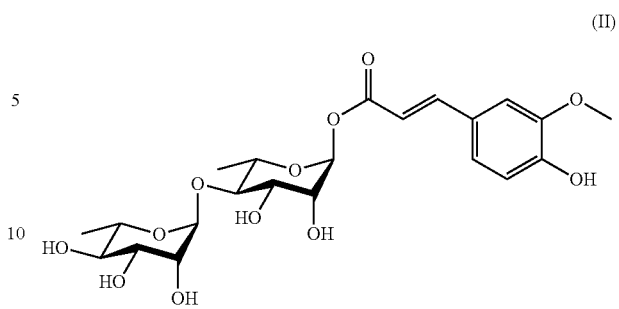

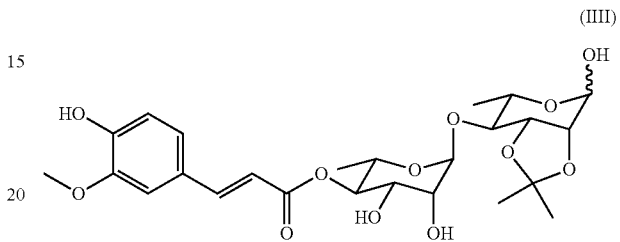

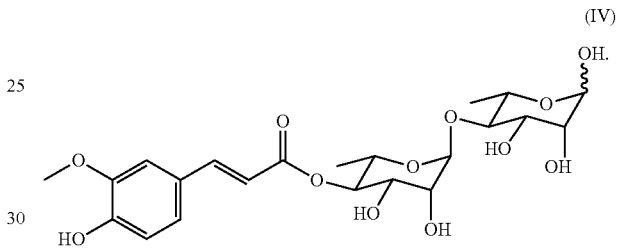

In another preferred embodiment, use of the compound represented by Formula (I) or an isomer, a solvate, a precursor, or a pharmaceutically acceptable salt thereof in the preparation of drugs or packs for preventing, alleviating, or treating neurodegenerative diseases, depression or stroke is provided.

In another preferred embodiment, the neurodegenerative diseases include:

neurodegenerative diseases characterized by neuroinflammation in the brain;

neurodegenerative diseases characterized by a significant increase in Aβ production;

neurodegenerative diseases characterized by a significant decline in learning and memory abilities; or neurodegenerative diseases characterized by a significant reduction in neural progenitor cells.

In another preferred embodiment, the neuroinflammation in the brain is characterized by a significant increase in the expression of inflammatory factors such as IL-6 and IL-1β.

In another preferred embodiment, the neurodegenerative diseases include: Alzheimer's disease, Parkinson's disease, and dementia with Lewy body (DLB).

In another aspect of the present invention, use of the compound represented by Formula (I) or an isomer, a solvate, a precursor, or a pharmaceutically acceptable salt thereof in the preparation of compositions, kits or packs for inhibiting neuroinflammation is provided.

In another aspect of the present invention, use of the compound represented by Formula (I) or an isomer, a solvate, a precursor, or a pharmaceutically acceptable salt thereof in the preparation of compositions, kits or packs for promoting the production of neural progenitor cells is provided.

In another aspect of the present invention, use of the compound represented by Formula (I) or an isomer, a solvate, a precursor, or a pharmaceutically acceptable salt thereof in the preparation of compositions, kits or packs for reducing Aβ production is provided.

In another aspect of the present invention, a pharmaceutical composition is provided, which comprises the compound represented by Formula (I) or an isomer, a solvate, a precursor, or a pharmaceutically acceptable salt thereof; and a pharmaceutically acceptable carrier.

In a preferred embodiment, the compound represented by Formula (I) or an isomer, a solvate, a precursor, or a pharmaceutically acceptable salt thereof is in an effective amount in the pharmaceutical composition. Preferably, the effective amount is 0.01-50% by weight, for example, but not limited to, 0.01-5%, 0.03-3%, 0.05-1%, 20-30%, and 40-50%, more preferably 0.03-30%, and further preferably 0.05-10%.

In another aspect of the present invention, the dosage forms of the pharmaceutical composition provided include: powder, pulvis, tablets, pills, capsules, sustained release preparations, controlled release preparations, injections, infusions, or suspensions.

In another aspect of the present invention, a pack is provided, which comprises the compound represented by Formula (I) or an isomer, a solvate, a precursor, or a pharmaceutically acceptable salt thereof or the pharmaceutical composition.

In another aspect of the present invention, a method for preventing, alleviating, or treating neurodegenerative diseases, depression or stroke is provided, the method comprises administering an effective amount of the compound represented by Formula (I) or an isomer, a solvate, a precursor, or a pharmaceutically acceptable salt thereof to a subject in need thereof.

In another aspect of the present invention, a method for preparing a compound represented by Formula II is provided; the method comprises the step of reacting di-rhamnopyranosylglycoside with tetrabutylammonium fluoride to obtain the compound represented by Formula (II).

(II)

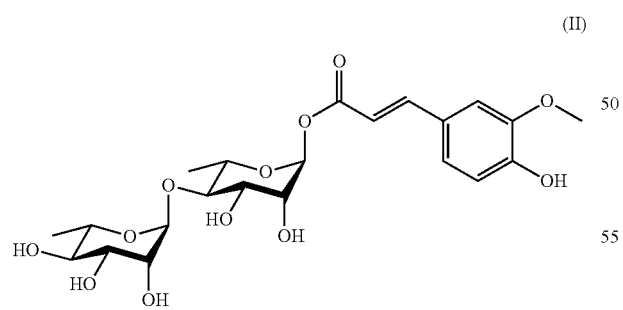

In another preferred embodiment, the di-rhamnopyranosylglycoside is obtained by reacting di-rhamnopyranosylthioglycoside with (4-O-tert-butyldimethylsilyl)-ferulic acid.

In another preferred embodiment, the di-rhamnopyranosylthioglycoside is obtained by reacting rhamnopyranosylthioglycoside with 2,3,4-O-triacetylrhamnosyl-1-O-trichloroacetimidate.

In another aspect of the present invention, a method for preparing a compound represented by Formula (III) or (IV) is provided, the method comprises the step of:

reducing the compound

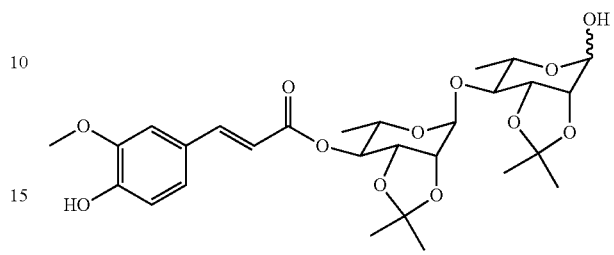

(more particularly, removing the isopropylidene protecting group of vicinal diol), to obtain the compound represented by Formula (III) or (IV).

In a preferred embodiment, the compound

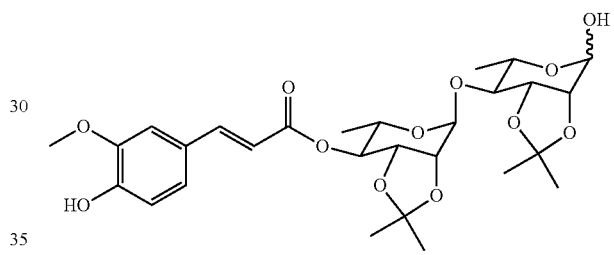

is obtained by the step of condensing the compound

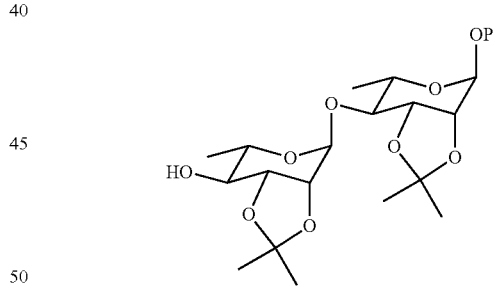

with the compound

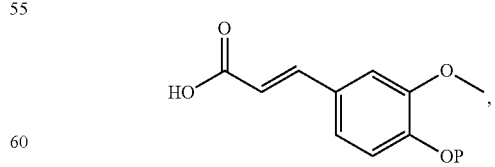

where P is H or a protecting group, preferably the protecting group is selected from the group consisting of: AII, Boc, TBS, Ac, Bn, PMB, and Cbz; and the protecting group can be reduced into H.

In another preferred embodiment, the compound

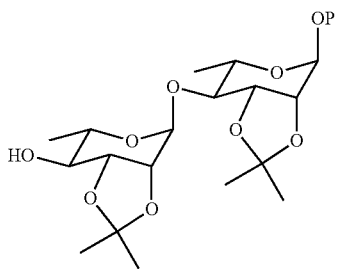

is obtained by the steps of subjecting the compound

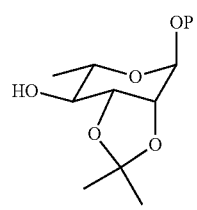

and the compound

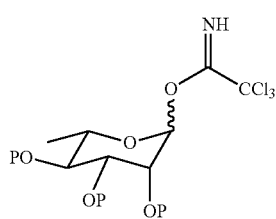

to an addition reaction and protecting the vicinal diol with the isopropylidene group.

Other aspects of the present invention will be apparent to those skilled in the art from the disclosure herein.

DETAILED DESCRIPTION

Figure 1:
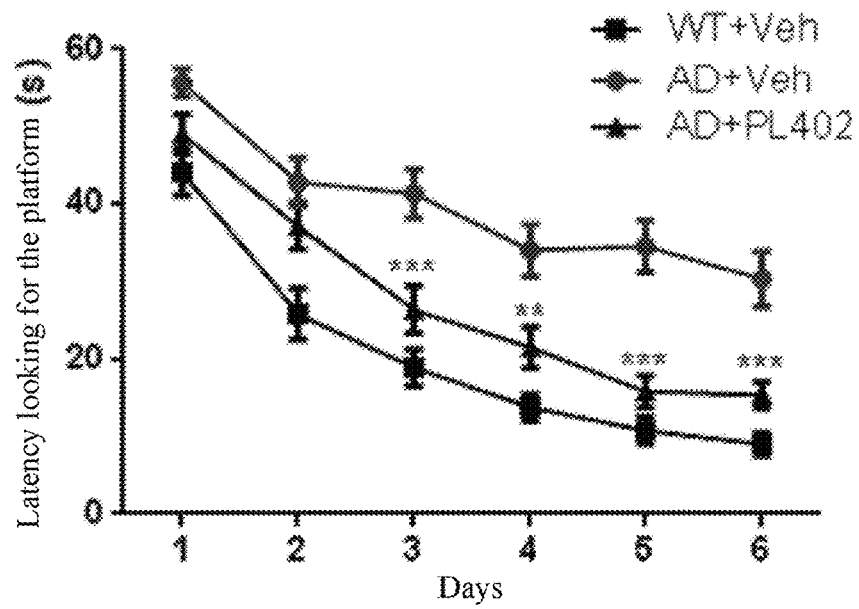
FIG. 1 shows the improvement of the Morris water maze index of AD mice by PL402.

After extensive research by the inventors, the compound of Formula (I) can significantly improve the symptoms of neurodegenerative diseases. In both in vitro and in vivo experiments, the compound of Formula (I) can effectively promote the proliferation of neural progenitor cells, which is not only preventive, but also can serve as a treatment approach to promote nerve regeneration to fight against cognition impairment associated with aging and neurodegenerative diseases.

Terms

The term "alkyl" as used herein refers to a linear or branched saturated aliphatic hydrocarbon group having 1-4 carbon atoms, preferably 1-2 carbon atoms. For example, the alkyl includes but is not limited to methyl, ethyl, n-propyl, isopropyl, n-butyl, isobutyl, and tert-butyl.

The term "alkenyl" as used herein includes a linear or branched hydrocarbon group having at least one carbon-carbon double bond and 2-4 carbon atoms, preferably 2-3 carbon atoms.

The term "alkynyl" as used herein includes a linear or branched hydrocarbon group having at least one carbon-carbon triple bond and 2-4 carbon atoms, preferably 2-3 carbon atoms.

The term "halo" as used herein refers to F, Cl, Br, or I.

The term "isomer" as used herein includes geometric isomers, enantiomers, and diastereomers, eg, cis-trans isomers, and conformational isomers.

The expression

as used herein is well known to those skilled in the art, and means a heterocyclic ring with an X atom. In a preferred implementation of the present invention, the

is a six-membered heterocyclic ring.

The expression

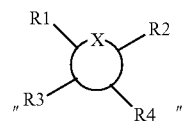

as used herein is well known to those skilled in the art, and means that the substitution with the optional R1-R4 groups occurs at any one or more positions on the ring that can be substituted. Also, at different substitution positions, the groups can be different.

The expression

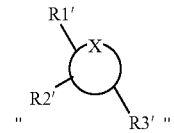

as used herein is well known to those skilled in the art, and means that the substitution with the optional R1'-R3' groups occurs at any one or more positions on the ring that can be substituted. Also, at different substitution positions, the groups can be different.

"P" as used herein is H or a protecting group, in which the protecting group is preferably selected from the group consisting of: AII, Boc, TBS, Ac, Bn, PMB, and Cbz; and the protecting group can be reduced into H.

Also, in different compounds, the protecting groups can be the same or different. Even in the same batch of reactions, the P group at different positions on different compounds or the same compound may also be different.

The term "solvate" as used herein refers to a compound that carries a solvent molecule, for example, the solvate may be a hydrate.

In the present invention, the term "contain/containing" means that various ingredients can be used together in the mixture or composition of the present invention. Therefore, the terms "consisting essentially of" and "consisting of" are included in the term "contain/containing".

In the present invention, "pharmaceutically acceptable" ingredient is the substance that is suitable for use with humans and/or animals without excessive adverse side effects, such as toxicity, irritation, and allergies, that is, having a reasonable benefit/risk ratio.

In the present invention, "pharmaceutically acceptable carrier" is a pharmaceutically or food acceptable solvent, suspending agent or excipient, which is used to deliver the compound of Formula (I) of the present invention, or an isomer, a solvate, a precursor, or a pharmaceutically acceptable salt thereof to animals or humans. The carrier may be liquid or solid.

Compound

The present invention provides a compound represented by structural Formula (I):

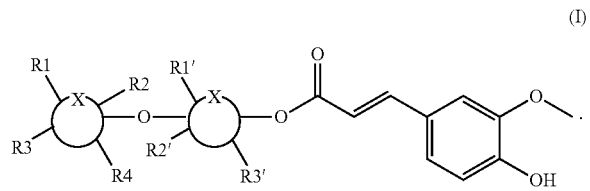
(I)

It is to be understood that in Formula (I), the position of X is a schematic position, and not limited to the side of R1 or R1' in the figure. It may also be present between R1 and R3, R3 and R4, R2 and the group

----O----, and R4 and the group

----O---- ;

and it may also be present between R2' and R3', R1' and

----O----,

R2' and

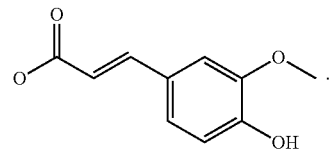

and R3' and the group

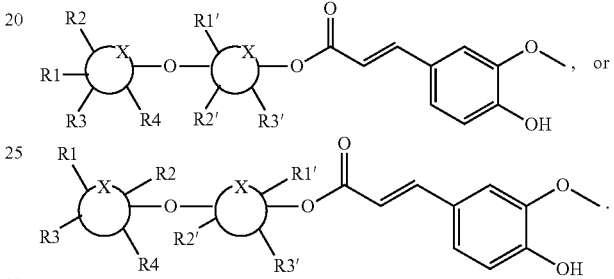

For example, the compound may be:

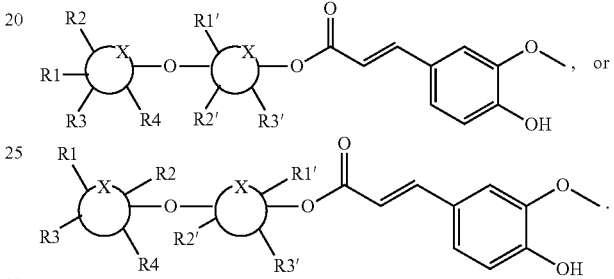

in which

is a six-membered heterocyclic ring, where X is O; R1-R4 are each independently selected from hydrogen, hydroxyl, C1-C4 alkyl, C2-C4 alkenyl, C2-C4 alkynyl, and halo, or adjacent two groups of R1-R4 are linked to each other to form a cyclic structure with the parent ring; and R1'-R3' are each independently selected from hydrogen, hydroxyl, C1-C4 alkyl, C2-C4 alkenyl, C2-C4 alkynyl, and halo, or adjacent two groups of R1'-R3' are linked to each other to form a cyclic structure with the parent ring.

In a preferred embodiment of the present invention, R1-R4 are each independently selected from hydrogen, hydroxyl, and C1-C2 alkyl, or adjacent two groups of R1-R4 are linked to each other to form a five-membered ring with the parent ring; and R1'-R3' are each independently selected from hydrogen, hydroxyl, and C1-C2 alkyl, or adjacent two groups of R1'-R3' are linked to each other to form a five-membered ring with the parent ring.

The present invention also includes an isomer, a solvate, a precursor, or a pharmaceutically acceptable salt of the compound of Formula (I), as long as they also have the same or substantially the same functions as the compound of Formula (I). The "pharmaceutically acceptable salt" refers to a salt formed by the reaction of the compound with an inorganic acid, an organic acid, an alkali metal or an alkaline earth metal. These salts include, but are not limited to, (1) salts with inorganic acids such as hydrochloric acid, sulfuric acid, nitric acid, and phosphoric acid; (2) salts with organic acids such as acetic acid, oxalic acid, succinic acid, tartaric acid, methanesulfonic acid, maleic acid, or arginine. Other salts include salts with alkali metals or alkaline earth metals (such as sodium, potassium, calcium, or magnesium), in the form of esters, carbamates, or other conventional "prodrugs". The compound has one or more asymmetric centers. Therefore, these compounds can exist as racemic mixtures, individual enantiomers, individual diastereomers, mixtures of diastereomers, cis- or trans-isomers.

The "precursor of the compound" refers to a precursor of the compound that is converted into the compound of structural Formula (I) or a salt or solution of the compound of structural Formula (I) by metabolic or chemical reactions in a patient after administration through an appropriate route.

In a preferred embodiment of the present invention, the five-membered ring is a heterocyclic ring containing an O atom; preferably, the five-membered ring contains two O atoms.

In a preferred embodiment of the present invention, the compound includes the compounds of Formulae (II)-(IV), among which the compound of Formula (II) is particularly preferred.

(II)

also designated as PL402;

(III)

also designated as PL404;

(IV)

also designated as PL405.

In an embodiment of the present invention, a method for preparing a compound of Formula II comprises:
Step 1: mixing 2,3,4-O-triacetylrhamnosyl-1-O-tricholoracetimidate and rhamnopyranosylthioglycoside and reacting to obtain a di-rhamnopyranosylthioglycoside product with a structure represented by Formula (V);

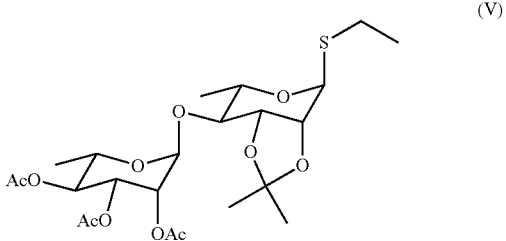 [SMILES: CCSC1OC(C)C(OC2OC(C)C(OC(C)=O)C(OC(C)=O)C2OC(C)=O)C2OC(C)(C)OC12]

(V)

Step 2: mixing the di-rhamnopyranosylthioglycoside product with a structure represented by Formula (V) and (4-O-tert-butyldimethylsilyl)-ferulic acid and reacting to obtain a di-rhamnopyranosylglycoside product with a structure represented by Formula VI;

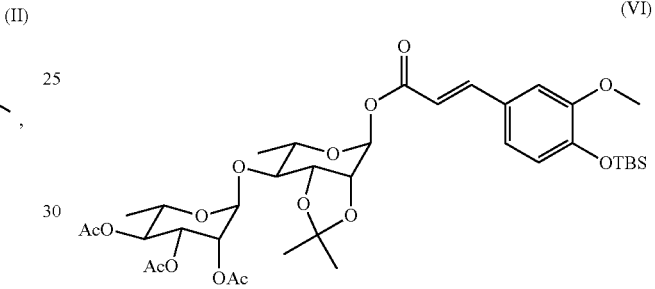

(VI)

Step 3: mixing the di-rhamnopyranosylglycoside product with a structure represented by Formula VI and tetrabutylammonium fluoride and reacting to obtain a product removed of tert-butyldimethylsilyl (TBS) and having a structure represented by Formula VII; and

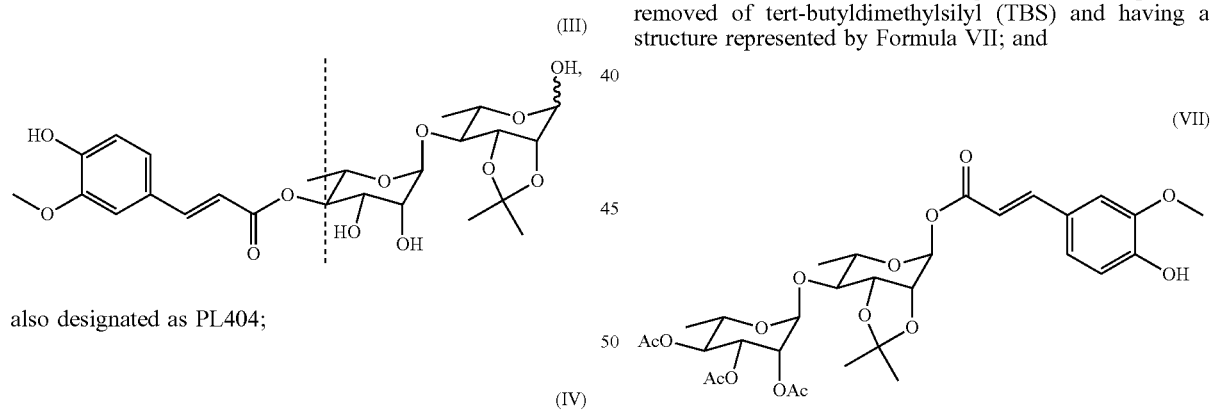

(VII)

Step 4: hydrolyzing the product removed of tert-butyldimethylsilyl (TBS) to obtain the compound of Formula II.

In one embodiment of the present invention, the reaction in Step 1) comprises adding 2,3,4-O-triacetylrhamnosyl-1-O-tricholoracetimidate dropwise to rhamnopyranosylthioglycoside at −78° C.

In one embodiment of the present invention, the reaction in Step 2) comprises adding di-rhamnopyranosylthioglycoside dropwise to (4-O-tert-butyl dim ethyl silyl)-ferulic acid at −78° C.

In one embodiment of the present invention, the mixing in Step 3) comprises adding tetrabutylammonium fluoride dropwise to the di-rhamnopyranosylglycoside product at room temperature.

In one embodiment of the present invention, a method for preparing a compound of Formula III or Formula IV comprises the steps of:

Step 1: subjecting the compound

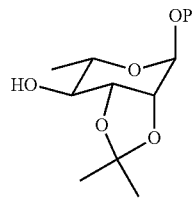

and the compound

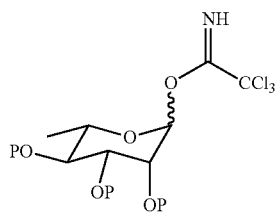

to an addition reaction, to obtain an addition product;

Step 2: protecting the vicinal diol on the addition product obtained in Step 1) with a isopropylidene group, to obtain a reaction product stable at a specific position;

Step 3: condensing the reaction product in Step 2) with

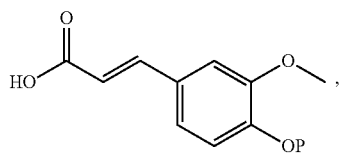

to obtain a condensation product; and

Step 4: reducing the condensation product, particularly removing the isopropylidene group protecting the vicinal diol, to obtain the compound represented by Formula (III) or (IV).

It is to be understood by those skilled in the art that after knowing the structure of the compound of the present invention, the compound of the present invention can be obtained by a variety of methods well known in the art using well-known raw materials, such as chemical synthesis or extraction from organisms (such as animals or plants), which are all included in the present invention.

The synthesized compound can be further purified by column chromatography, high performance liquid chromatography and other methods.

Use

The inventors found that the compound of Formula (I) of the present invention can significantly improve the symptoms of neurodegenerative diseases and is also effective for depression and stroke. The compound of the present invention can inhibit neuroinflammation, reduce Aβ production, and promote the production of neural progenitor cells. The experimental results have demonstrated that the compound of the present invention significantly improves the learning and memory ability of animals. The increase of neural progenitor cells will further promote the increase of neurons.

The whole process is known as neurogenesis. According to the mechanism of the compound of the present invention, it can increase the neural progenitor cells, so it is also effective for Huntington's disease, and amyotrophic lateral sclerosis. According to the mechanism of the compound of the present invention, it is also effective for depression and stroke. In the pathogenesis of depression or stroke, the occurrence of neuroinflammation in the brain is also involved, which in turn causes reduction in neural progenitor cells and changes in neural function. The compound of Formula (I) of the present invention can increase neural progenitor cells, and thus is also effective for depression and stroke.

Based on the new findings of the inventors, the present invention provides use of the compound represented by Formula (I) or an isomer, a solvate, a precursor, or a pharmaceutically acceptable salt thereof in the preparation of drugs or packs for preventing, alleviating, or treating neurodegenerative diseases, depression or stroke.

The present invention also provides use of the compound represented by Formula (I) or an isomer, a solvate, a precursor, or a pharmaceutically acceptable salt thereof in the preparation of compositions, kits or packs for inhibiting neuroinflammation.

The present invention also provides use of the compound represented by Formula (I) or an isomer, a solvate, a precursor, or a pharmaceutically acceptable salt thereof in the preparation of compositions, kits or packs for promoting the production of neural progenitor cells.

The present invention also provides use of the compound represented by Formula (I) or an isomer, a solvate, a precursor, or a pharmaceutically acceptable salt thereof in the preparation of compositions, kits or packs for reducing Aβ production.

Pharmaceutical Composition

The present invention also provides a pharmaceutical composition comprising: (a) an effective amount of a compound of Formula (I), or an isomer, a solvate, a precursor, or a pharmaceutically acceptable salt thereof; and (b) a pharmaceutically acceptable carrier or excipient.

In the pharmaceutical composition of the present invention, the compound represented by Formula (I) or an isomer, a solvate, a precursor, or a pharmaceutically acceptable salt thereof is in an effective amount. For example, the compound represented by Formula (I) or a pharmaceutically acceptable salt thereof may be contained in an amount of 0.001-50% by weight. Preferably, the pharmaceutical composition comprises 0.01-20% by weight of the compound represented by Formula (I) or a pharmaceutically acceptable salt thereof.

The pharmaceutical composition according to the present invention may be in various dosage forms, as long as the dosage form can enable the active ingredient to effectively reach desired sites in the mammalians. For example, the dosage form can be selected from powder, pulvis, tablets, pills, capsules, sustained release preparations, controlled release preparations, injections, infusions, or suspensions. According to the types of diseases to be treated by the compound of the present invention, the dosage form that is convenient for application can be used by those skilled in the art.

For ease of preparation and storage, the pharmaceutical composition is preferably a solid composition, especially tablets and solid or liquid filled capsules. For ease of administration, the pharmaceutical composition is preferably an oral preparation. The compound of the present invention or its pharmaceutical composition can also be stored in a sterilized device suitable for injection or infusion.

The effective dosage of the compound of Formula (I) as an active ingredient may vary depending on the mode of administration and the severity of disease to be treated. However, in general, when the compound of the present invention is administered at a dose of about 0.01-100 mg/kg of body weight per day, satisfactory results can be obtained. Preferably, the compound of the present invention is administered at 1-3 divided doses per day, or administered in a sustained release dosage form. This dosage regimen can be adjusted to provide an optimum therapeutic response. For example, due to the urgent demands of the therapeutic status, several divided doses can be given daily, or the dose can be reduced proportionally.

The present invention will be further described below in conjunction with specific examples. It is to be understood that these examples are merely illustrative of the present invention and are not intended to limit the scope of the present invention. The experimental methods not specifically specified in the following examples are generally carried out according to conventional conditions, for example those described in J. Sambrook eds, Molecular cloning: A Laboratory manuals, 3rd Edition, Science Press, 2002, or in accordance with the conditions suggested by the manufacturer.

Statistical Analysis of Data

In the following examples, all experimental data is expressed as mean±standard error. T test is used for comparison between different treatment groups. One-way ANOVA is used to analyze the results between multiple groups, and post hoc test is performed using Fisher's protected least significant difference test or Bonferronit test; or two-way ANOVA is used for analysis, and Tukey post hoc test is used for post hoc test. When P<0.05, there is a significant difference between the groups.

Example 1: Synthesis of Compound PL402

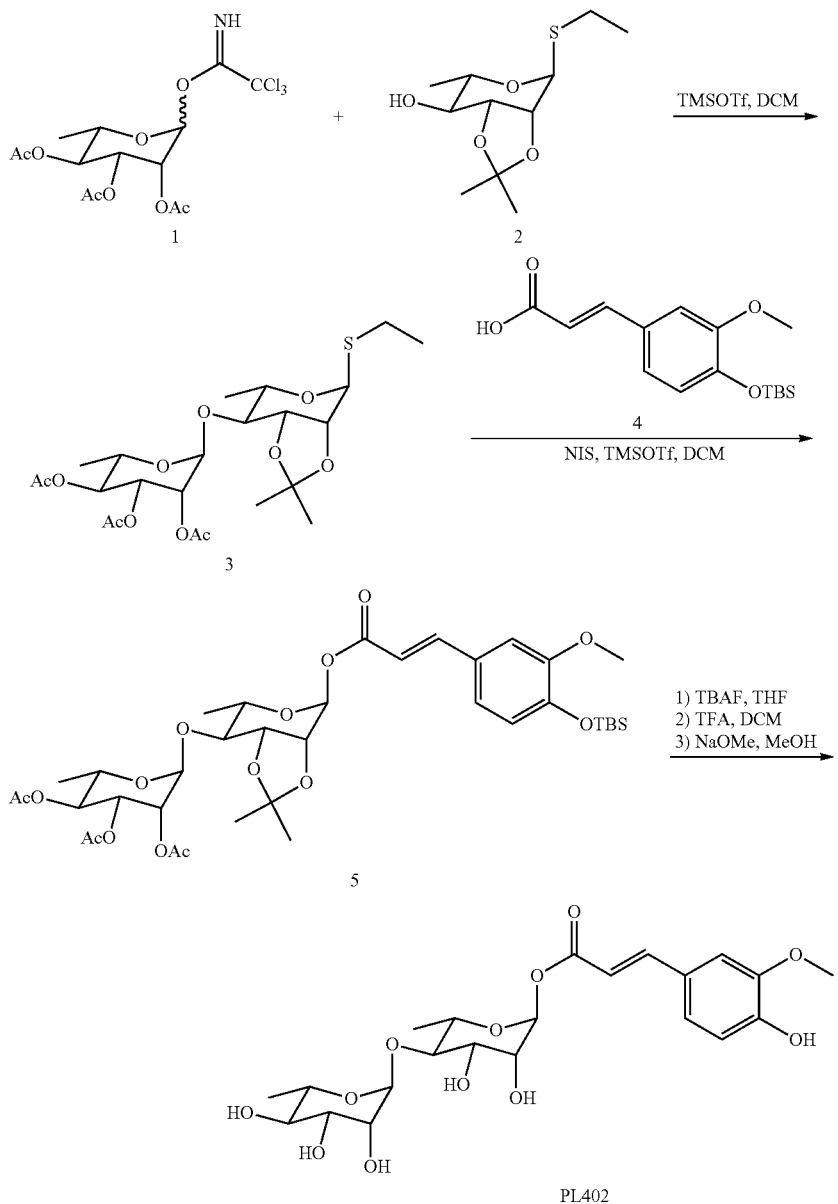

PL402

1. Preparation of Compound 3

Following the method as described in J. Chem. Soc., Perkin Trans. 1, 2000, 1445-1453, Compound 2 (248 mg, 1.0 mmol) (Organic and Biomolecular Chemistry, 2014, vol. 12, #7, p. 1114-1123), dry 4 Å molecular sieve (250 mg) and $CH_2Cl_2$ (12 mL) were added to a dry reaction flask, and stirred for 10 min at room temperature. After cooling to −78° C., a solution of trimethylsilyl triflate (TMSOTf) (0.036 mL, 0.2 mmol) in $CH_2Cl_2$ and a solution of Compound 1 (521 mg, 1.2 mmol) (Journal of the American Chemical Society, 2000, vol. 122, #41, p. 9939-9953) in $CH_2Cl_2$ (2 mL) were added. After 30 min, 0.1 mL $Et_3N$ was added to terminate the reaction. The reaction solution was filtered, concentrated, and purified by column chromatography (petroleum ether:ethyl acetate=3:1) to obtain Compound 3 (468 g, 0.9 mmol, yield 90%).

1H NMR (300 MHz; $CDCl_3$) 5.51 (s, 1H), 5.33 (d, 1H, J=1.7 Hz), 5.30 (dd, 1H, J=1.9 Hz, 3.3), 5.22 (dd, 1H, $J_1$=3.3 Hz, $J_2$=10.1 Hz), 5.08 (t, 1H, J=10.0 Hz), 4.21-4.13 (m, 2H), 4.06 (m, 1H), 3.89 (m, 1H), 3.56 (dd, 1H, h=7.1 Hz, $J_2$=9.9 Hz), 2.61 (m, 2H), 2.15 (s, 1H), 2.05 (s, 1H), 1.98 (s, 1H), 1.53 (s, 1H), 1.32 (s, 1H), 1.34-1.21 (m, 9H); ESI-MS m/z 521 (M+1)$^+$.

2. Preparation of Compound 5

Compound 4

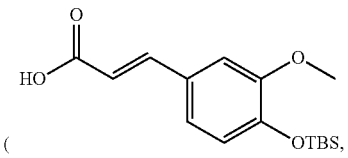

308 mg, 1.0 mmol) and 4 Å molecular sieve were mixed in dry $CH_2Cl_2$ (20 mL), stirred at room temperature for 30 min, then cooled to −78° C., and stirred for additional 30 min. N-iodosuccinimide (NIS) (225 mg, 1.0 mmol) and TMSOTf (0.018 mL, 0.1 mmol) were added in sequence. Finally, Compound 3 (312 mg, 0.6 mmol) dissolved in dry $CH_2Cl_2$ (DCM, 20 mL) was added dropwise to the reaction, stirred at −78° C. for 20 min, slowly returned to room temperature and stirred. After 2 hours, saturated $Na_2S_2O_3$ and $NaHCO_3$ solutions were added to quench the reaction, filtered, extracted with ethyl acetate, washed with saturated saline, dried over anhydrous $Na_2SO_4$, filtered, concentrated, and purified by column chromatography (petroleum ether:ethyl acetate=3:1), to obtain Compound 5 as a white solid (368 mg, 0.48 mmol, yield 80%).

1H NMR (400 MHz; $CDCl_3$) 7.52 (d, 1H, J=12 Hz), 6.09-6.88 (m, 2H), 6.69 (d, 1H, J=8 Hz), 6.24 (s, 1H), 6.14 (d, 1H, J=8 Hz), 5.20-5.15 (m, 2H), 5.03 (d, 1H, J=8 Hz), 4.93-4.90 (m, 1H), 4.14 (dd, 1H, $J_1$=4 Hz, $J_2$=8 Hz), 3.99 (d, 1H, J=4 Hz), 3.37-3.69 (m, 2H), 3.68 (s, 3H), 3.43 (dd, 1H, $J_1$=4 Hz, $J_2$=8 Hz), 1.98 (s, 3H), 1.89 (s, 3H), 1.81 (s, 3H), 1.38 (s, 3H), 1.15 (s, 3H), 1.11-1.05 (m, 6H), 0.82 (s, 9H), 0 (s, 6H); ESI-MS m/z 767 (M+1)$^+$.

Figure 7:
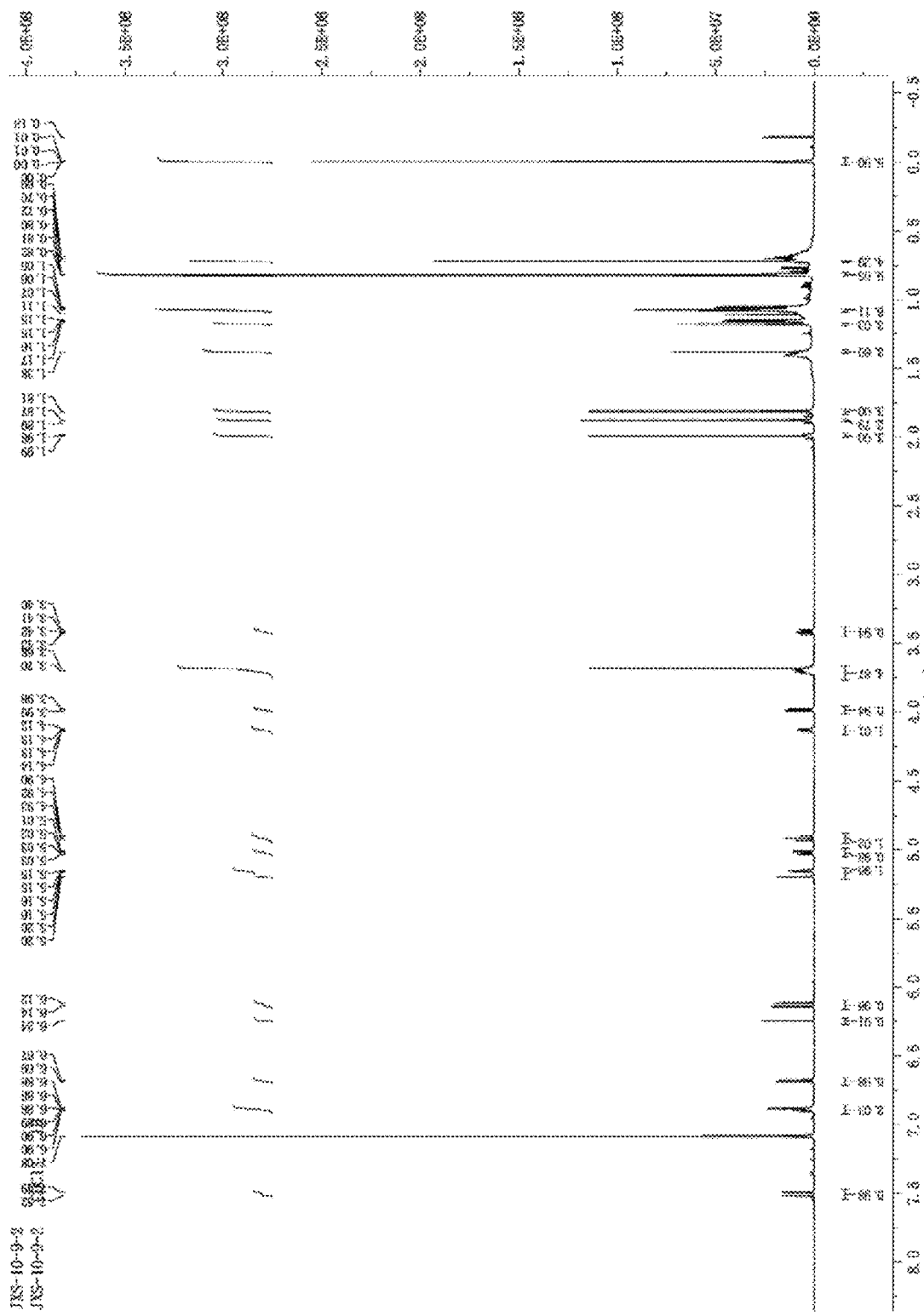
FIG. 7 shows the identification of Compound 5.

The identification of Compound 5 is shown in FIG. 7.

3. Preparation of Compound PL402

Compound 5 (306 mg, 0.4 mmol) was dissolved in tetrahydrofuran (8 mL) and acetic acid (16 μL, 1.12 mmol), and 1 M solution of tetrabutyl fluoride (TBAF) in tetrahydrofuran (THF) (0.54 mL, 0.54 mmol) was added with magnetic stirring at room temperature. After reaction at room temperature for 3.5 hours, the reaction solution was diluted with ethyl acetate (30 mL), distilled, and washed with water, saturated $NaHCO_3$ solution, and brine, and dried over anhydrous $Na_2SO_4$. Filtering and rotary drying gave a crude product (235 mg), which was directly used in the next step.

To a reaction flask containing the product (235 mg, 0.36 mmol) of the previous step, a solution of trifluoroacetic acid (TFA) dissolved in $CH_2Cl_2$ (2:25, 5 mL) was added, the reaction was stirred at room temperature for 1 hour and then stopped. Aqueous NaOH solution (5 mL, 1 M) was added in an ice bath to quench the reaction, extracted with $CH_2Cl_2$, and dried over anhydrous $Na_2SO_4$. Filtering and rotary drying gave a crude product (165 mg), which was directly used in the next step.

The product of the previous step (165 mg, 0.27 mmol) was dissolved in a mixed solution (8 mL) of anhydrous $CH_3OH$ and anhydrous $CH_2Cl_2$ (1:1), and a catalytic amount of sodium methoxide (0.2 eq.) was added to adjust the pH to 9-10. The reaction was stirred at 40° C. for 5 hours, and an acidic cationic resin was added to neutralize the reaction solution to neutrality. Filtration and concentration gave a white solid product. The product was dissolved in water (1 mL), and purified by reverse-phase chromatography on silica gel to obtain Compound PL402 (78 mg, 0.16 mmol, yield of three steps: 40%).

1H NMR (400 MHz; MeOD) 7.683 (d, 1H, J=15.6 Hz), 7.229 (d, 1H, J=1.6 Hz), 7.114 (dd, 1H, 1=1.6 Hz, $J_2$=8 Hz), 6.829 (d, 1H, J=8.8 Hz), 6.407 (d, 1H, J=15.6 Hz), 6.403 (d, 1H, J=1.6 Hz), 5.231 (d, 1H, J=1.6 Hz), 3.994 (q, 1H, J=2 Hz), 3.896 (s, 3H), 3.880 (s, 1H), 3.845-3.831 (m, 1H), 3.777-3.700 (m, 2H), 3.650-3.621 (m, 2H), 3.431-3.408 (m, 1H), 1.319 (d, 3H, J=6 Hz), 1268 (d, 3H, J=6.4 Hz); ESI-MS m/z 487 (M+1)$^+$.

Figure 8:
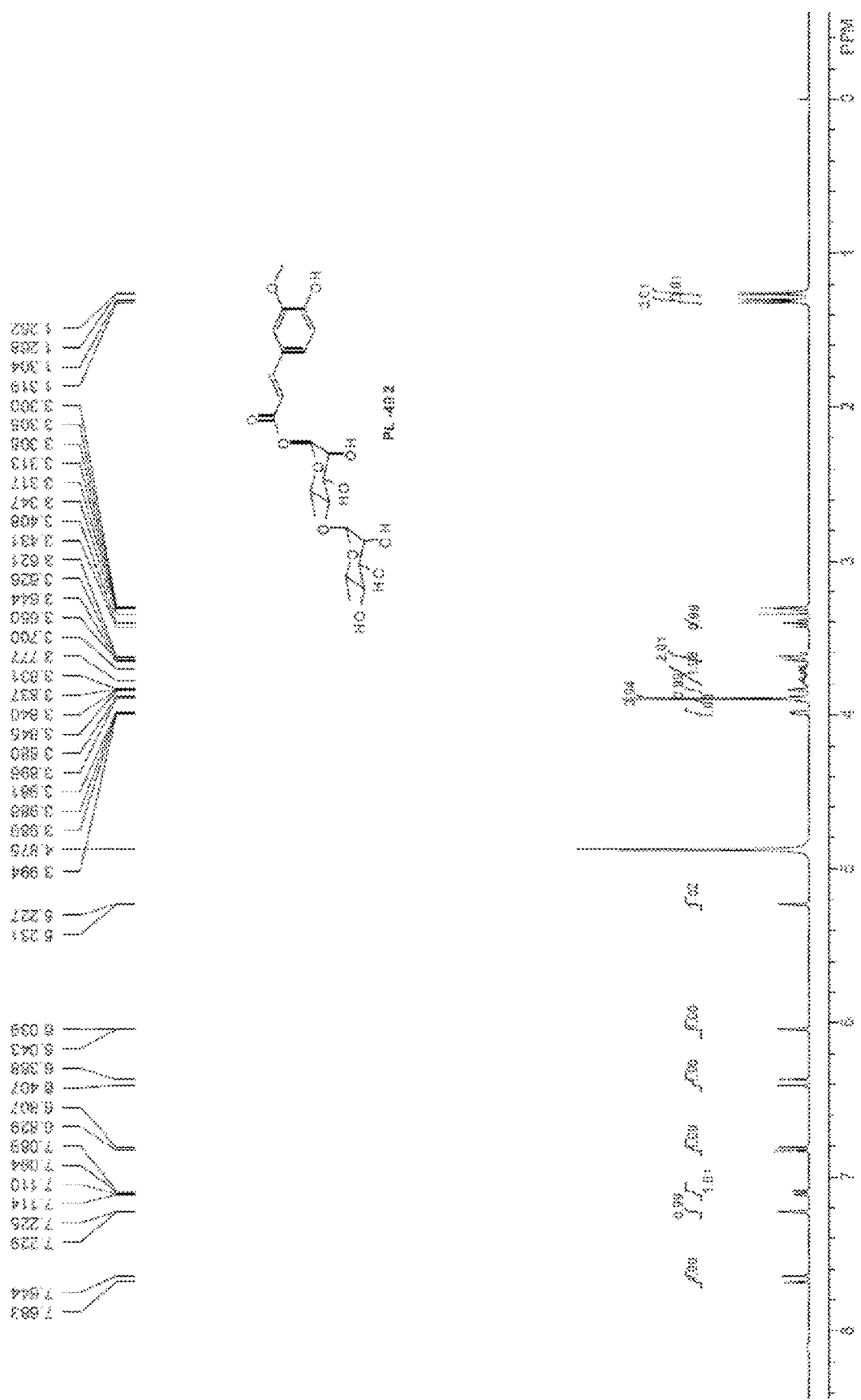
FIG. 8 shows the identification of PL402.

The identification of PL402 is shown in FIG. 8.

Example 2. Synthesis of Compounds PL404 and PL405

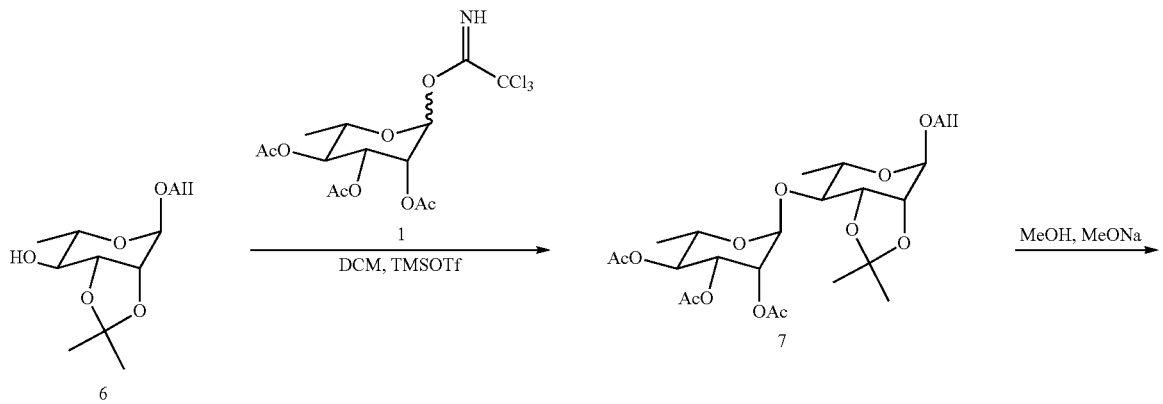

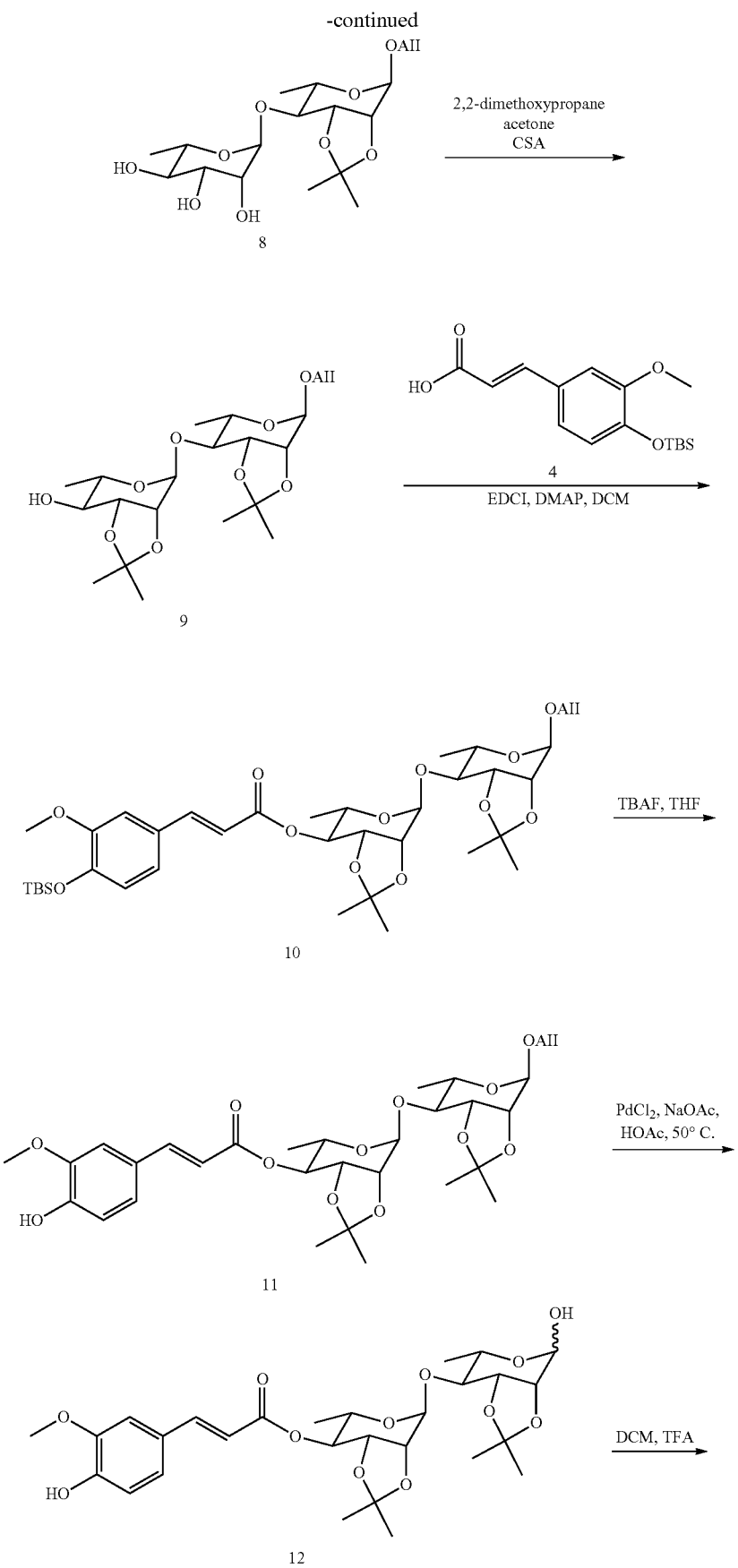

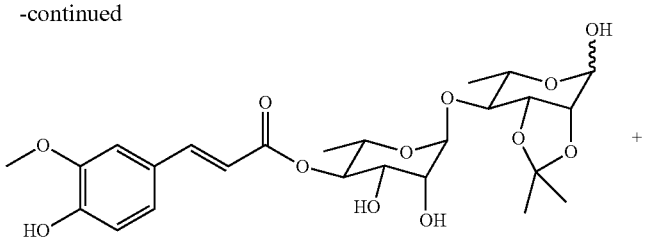

PL404

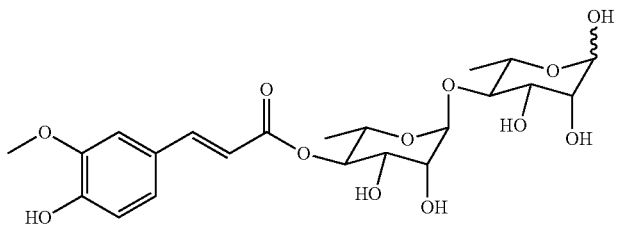

PL405

1. Preparation of Compound 7

Compound 6 (12.2 g, 5 mmol) (Chemistry—A European Journal, 21(29), 10416-10430; 2015), dry 4 Å molecular sieve (20 g) and CH2Cl2 (1.5 L) were added to a dry reaction flask, stirred at room temperature for 20 min, and cooled to −78° C. A solution of trimethylsilyl triflate (TMSOTf) (0.18 mL, 1 mmol) in $CH_2Cl_2$ and a solution of Compound 1 (25.6 g, 60 mmol) (Journal of the American Chemical Society, 2000, vol. 122, #41, p. 9939-9953) in CH2Cl2 (2.5 L) were added. After 30 min, 0.5 mL Et3N was added to terminate the reaction. The reaction solution was filtered, concentrated, and purified by column chromatography (petroleum ether:ethyl acetate=10:1 to 3:1) to obtain Compound 7 (21.9 g, 42.4 mmol, yield 85%). ESI-MS m/z 517 (M+1)$^+$.

2. Preparation of Compound 8

Compound 7 (21.9 g, 42.4 mmol) was dissolved in a mixed solution (2 L) of anhydrous CH3OH and anhydrous CH2Cl2 (1:1), and a catalytic amount of sodium methoxide (0.2 eq.) was added to adjust the pH to 9-10. The reaction was stirred at 40° C. for 4 hours, and an acidic cationic resin was added to neutralize the reaction solution to neutrality. The reaction solution was filtered, concentrated, and purified by column chromatography (petroleum ether:ethyl acetate=10:1 to 1:1) to obtain Compound 8 (11.6 g, 29.7 mmol, yield 70%). ESI-MS m/z 391 (M+1)$^+$.

3. Preparation of Compound 9

To a 1 L three-neck flask, Compound 8 (11.6 g, 29.7 mmol), acetone (120 ml), p-toluenesulfonic acid (116 mg, 1% w/w), and then 2,2-dimethoxypropane (9.3 g, 89.4 mmol) were added. The reaction was reacted at 15-20° C. for 1 hour, until TLC showed that the reaction was complete. Triethyl amine (24 ml) was added to the reaction solution, and then the reaction solution was concentrated, dried, and purified by column chromatography (petroleum ether:ethyl acetate=20:1 to 5:1) to obtain Compound 9 (8.9 g, 20.7 mmol, yield 70%). ESI-MS m/z 431 (M+1)$^+$.

4. Preparation of Compound 10

To a 1 L three-neck flask, Compound 9 (8.9 g, 20.7 mmol), dichloromethane (500 ml), and Compound 4 (9.6 g, 30.2 mmol) were added. Then, DIEA (10.7 g, 82.9 mmol), EDCI.HCl (7.9 g, 41.1 mmol), DMAP (0.3 g, 2.5 mmol), and DIEA (6.7 g, 51.9 mmol) were added in sequence. The reaction solution was stirred at 15-20° C. for 18 hours, and then the organic phase was washed with saturated saline (50 ml), concentrated under reduced pressure, and purified by column chromatography (petroleum ether:ethyl acetate=10:1 to 2:1) to obtain Compound 10 (10 g, 13.9 mmol, yield 70%).

ESI-MS m/z 721 (M+1)$^+$.

5. Preparation of Compound 11

To a 500 ml three-neck flask, THF (100 ml), Compound 10 (10 g, 13.9 mmol), and Compound TABF (25 ml, 1 mol/L solution in THF) were added. The reaction was carried out at 10-20° C. until TLC showed that the reaction was complete. The reaction solution was added to water (200 ml), and extracted with ethyl acetate (200 ml*3). The organic phases were combined, washed with saturated brine (200 ml*6), dried over anhydrous sodium sulfate, filtered, concentrated, and purified by column chromatography (petroleum ether:ethyl acetate=10:1 to 3:1) to obtain Compound 11 (4.2 g, 6.9 mmol, yield 50%).

ESI-MS m/z 607 (M+1)$^+$.

6. Preparation of Compound 12

To a 1 L three-neck flask, Compound 11 (4.2 g, 6.9 mmol), acetic acid (100 ml), water (5 ml), NaOAc (37.5 g, 276 mmol), and PdCl2 (2.0 g, 11.3 mmol) were added. The reaction solution was stirred at 15-20° C. for 40 h. The reaction solution was filtered, concentrated, and purified by column chromatography (petroleum ether:ethyl acetate=10:1 to 1:1) to obtain Compound 12 (2.35 g, 4.2 mmol, yield 60%).

ESI-MS m/z 567 (M+1)$^+$.

7. Preparation of PL404 and PL405

To a 500 ml three-neck flask, Compound 12 (2.35 g, 4.2 mmol), dichloromethane (28 ml), and TFA (2.4 g, 21 mmol) were added. The reaction solution was stirred at 15-20° C. for 20 min, cooled to 0° C.-5° C., adjusted to pH 8-9 with a saturated sodium bicarbonate solution, and separated. The organic phase was concentrated, and purified by column chromatography (petroleum ether:ethyl acetate=20:1 to 1:1)

to obtain Compound PL404 (273 mg, 0.52 mmol) and PL405 (200 mg, 0.41 mmol).

PL404:

1H NMR (400 MHz; CDC13) 7.689 (d, 1H, J=15.6 Hz), 7.081 (dd, 1H, J1=1.6 Hz, J2=8 Hz), 7.034 (s, 1H), 6.936 (d, 1H, J=13.6 Hz), 6.339 (d, 1H, J=16 Hz), 5.372 (d, 0.7H, J=6 Hz), 5.086 (s, 1H), 4.99 (d, 0.3H, J=6 Hz), 4.86-4.80 (m, 1H), 4.768 (d, 0.7H, J=6 Hz), 4.695 (d, 0.3H, J=6 Hz), 4.609 (d, 0.7H, J=6 Hz), 4.524 (d, 0.3H, J=6 Hz), 4.028-4.008 (m, 2H), 3.981-3.896 (m, 6H), 1.446-1.223 (m, 12H); ESI-MS m/z 527 (M+1)$^+$.

Figure 9:
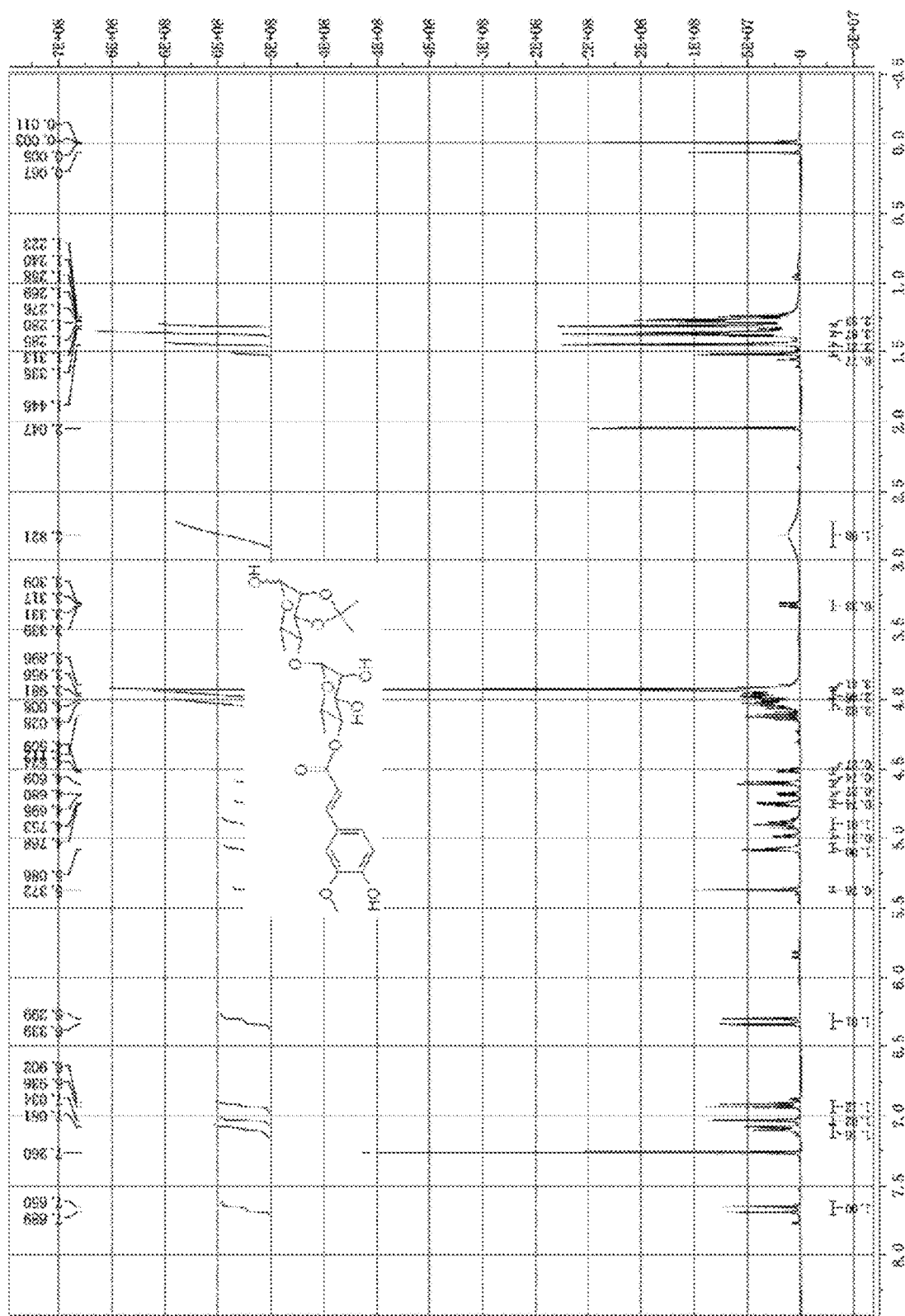
FIG. 9 shows the identification of PL404.

The identification of PL404 is shown in FIG. 9.

PL405:

1H NMR (400 MHz; MeOD) 7.67 (dd, 1H, J1=4 Hz, J2=8 Hz), 7.21 (s, 1H, J=1.6 Hz), 7.09 (dd, 1H, J1=1.6 Hz, J2=8 Hz), 6.81 (d, 1H, J=8 Hz), 6.43 (dd, 1H, J1=4 Hz, J2=12 Hz), 5.26 (d, 1H, J=4 Hz), 5.05 (t, 1H, J=8 Hz), 5.00 (s, 0.5H), 4.72 (s, 0.5H), 4.04-4.00 (m, 1H), 3.95-3.93 (m, 1H), 3.89 (s, 3H), 3.88-3.85 (m, 2H), 3.77-3.75 (m, 1H), 3.55-3.50 (m, 0.5H), 3.48-3.45 (m, 1H), 3.34-3.31 (m, 0.5H), 1.33 (d, 1H, J=4 Hz), 1.30 (d, 2H, J=4 Hz), 1.27 (d, 3H, J=4 Hz); ESI-MS m/z 487 (M+1)$^+$.

Figure 10:
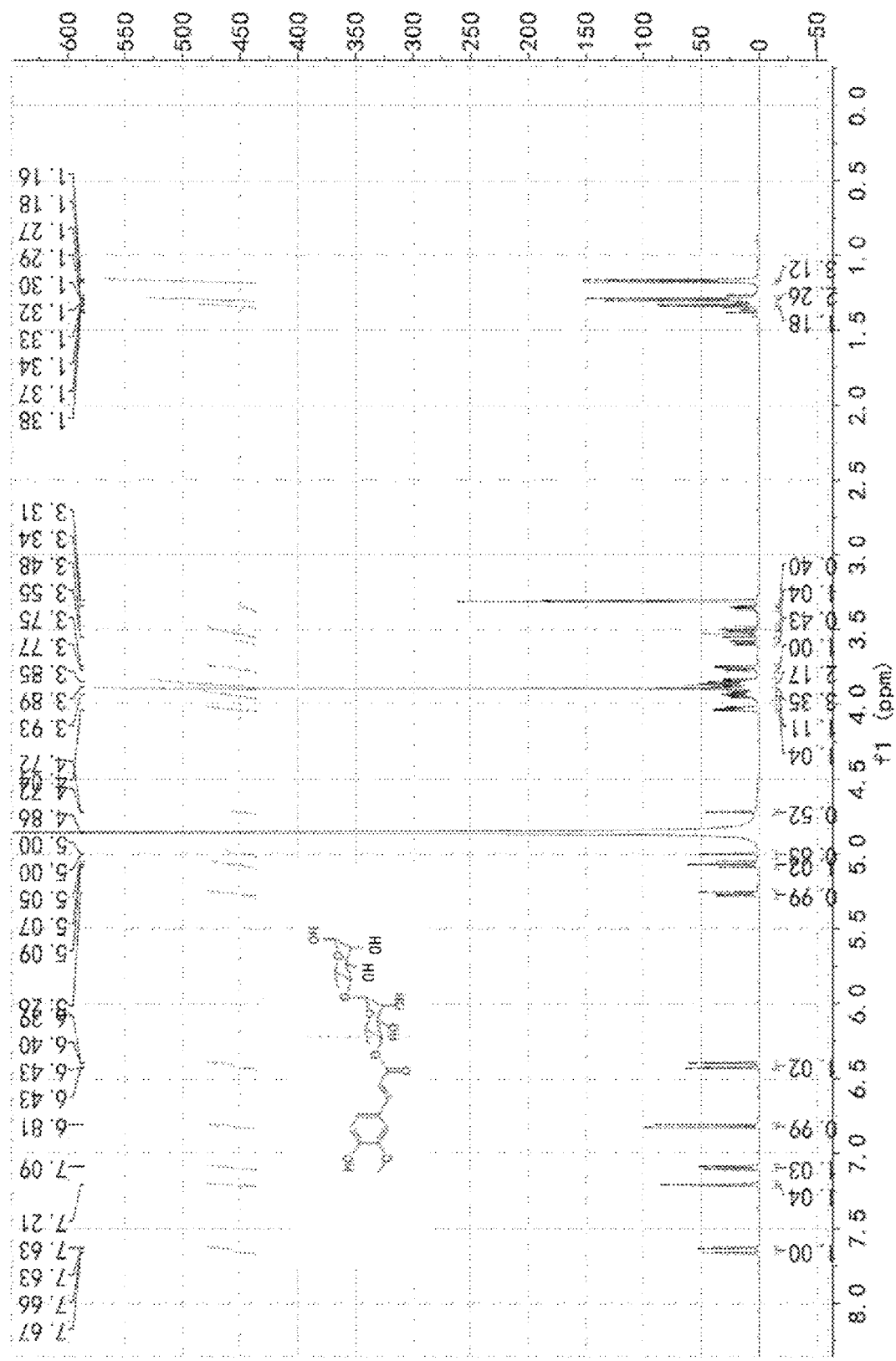
FIG. 10 shows the identification of PL405.

The identification of PL405 is shown in FIG. 10.

Example 3. Improvement of Learning and Memory of AD Mice by PL402

1. Morris Water Maze Experiment

Twenty 5-6-month-old APP/PS1 transgenic male mice (AD mice) were selected and divided into a model group and a polysaccharide administration group according to the random number table method. PL402 was administered daily by intragastric administration (50 mg/kg), and 10 non-transgenic mice were used in a negative control group (without administration). After 90 days of consecutive administration, Morris water maze behavior test was used to detect the effect of PL402 on the learning and cognitive functions of APP/PS1 mice.

In this experiment, a classic Morris water maze test procedure was used, which includes a place navigation test and a space exploration test. The duration of the experiment was 7 days in total, and the space exploration test was introduced at Days 4 and 7.

From the experimental results shown in FIG. 1, it can be seen that in this place navigation test, all the three groups of animals after training for 3 days have a shortened escape latency, indicating that each mouse can successfully complete the space learning task in the water maze. The escape latency is taken as a detection index.

The results showed that the mice in the negative control group respond more quickly, and they can spend less time in locating the platform after entering the water. With the increase of training times, the latency to reach the platform is shortened. In contrast, the mice in the model group are slow in response, circle along the barrel wall after entering the water, and have no escape behaviors. After artificially leading them to the platform, they jump into the water again. After repeated trainings, they finally find the platform, but the time spend in looking for the platform is significantly prolonged. The ability of the mice in PL402 administration group to look for the platform is increasingly enhanced with the increase of the number of training. The mice in the three groups all have certain spatial memory. The latency to reach the platform of the model group is longer than that of the control group, indicating that the learning and memory abilities of mice in the model group decline, and the model mice have better simulated the learning and memory impairments in AD. Compared with the model group, the latency of mice in PL402 administration group has statistically significant decrease, which shows that the learning and memory abilities of AD mice after administration of PL402 are significantly improved.

2. Treatment with 5-Bromo-2'-Deoxyuridine (BrdU)

In the administration experiment of 5-6-month-old AD mice, each mouse was given 100 μl of PL402 by intragastric administration at a dosage of 50 mg/kg of body weight. A control group was set, and the mice were given 100 μl of water by intragastric administration once a day. The administration was continued for 90 days, and intraperitoneal injection of 5-bromo-2'-deoxyuridine (BrdU) at a dosage of 50 mg/kg of body weight was performed once a day for 7 days in total from Day 60. After 90 days of administration, the mice were anaesthetized and then perfused with paraformaldehyde (PFA), and then the whole brain was taken for further experiments.

Example 4. The Inhibition of Neuroinflammation by PL402

Neuroinflammation in the brain of AD is one of the causes of cognitive decline. Microglia are key cells that mediate neuroinflammation. The inventors studied whether PL402 is effective in inhibiting neuroinflammation by detecting the expression of inflammatory factors on mouse BV-2 cells.

BV-2 cells culture and stimulation: BV-2 cells were cultured in DMEM, plated in a 24-well plate and cultured for 24 hours. Then PL402 (0, 10, 30, 100, or 300 μM) and LPS (300 ng/ml) were added, and then incubated for 24 hours. RNA was extracted with Trizol, and the expression of related inflammatory factors was detected by QPCR.

Figure 2:
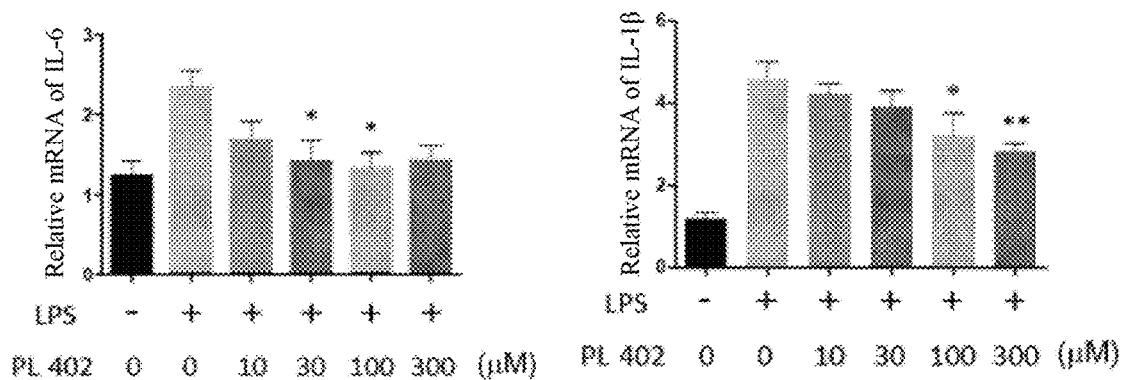
FIG. 2 shows the inhibition of neuroinflammation by PL402.

The results show that treatment with PL402 can significantly inhibit the expression of inflammatory factors IL-6 and IL-1β, as shown in FIG. 2.

Example 5. The Reduction of Aβ Production by PL402

Aβ is the main pathogenic protein of AD. The inventors investigated whether PL402 has an effect on inhibiting Aβ production by detecting the level of Aβ in neuroblastoma cells SK—N—SH cells (which can secrete Aβ).

Culture of SK—N—SH and detection of Aβ: SK—N—SH cells were cultured in DMEM, plated in a 24-well plate and cultured for 24 hours. PL402 (0, 10, 30, 100, or 300 μM) was added, and then incubated for 24 hours. The supernatant was collected and the total Aβ protein level was detected by ELISA.

Figure 3:
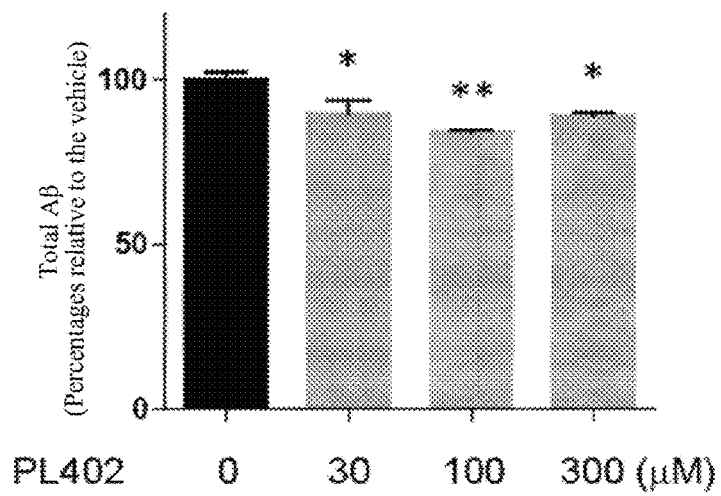
FIG. 3 shows the reduction of Aβ production by PL402.

The results show that treatment with PL402 can significantly inhibit the production of Aβ, as shown in FIG. 3. The inhibition effect is most desirable when PL402 concentration is 100 μM.

Example 6. Effect of PL404 on Learning and Memory Abilities of Animals

The selection of animals and the "Morris water maze experiment" was performed as described in Example 3, to detect the effect of PL404 on the animal learning and memory abilities.

Figure 4:
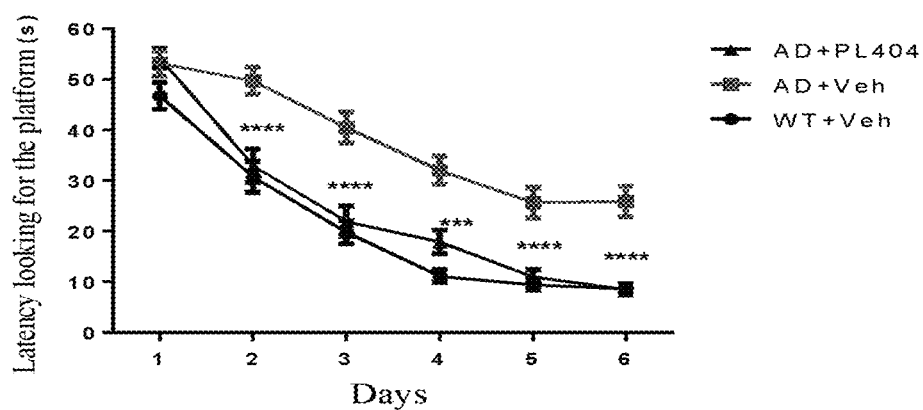
FIG. 4 shows the effect of PL404 on the learning and memory of animals.

The results are shown in FIG. 4. The latency of the mice in PL402 administration group was significantly different from that in the model group, and this difference is statistically significant.

Therefore, the learning and memory abilities of AD mice after administration of PL404 are significantly improved.

Example 7. Effect of PL404 on the Proliferation of Human Neural Progenitor Cells The inventors investigated whether PL404 has the effect on promoting proliferation by detecting the EdU incorporation of a human neural progenitor cell (differentiated by humanized iPSC). The dosage of PL404 was 0, 1, 3, 10, 30, or 100 μM.

Figure 5:
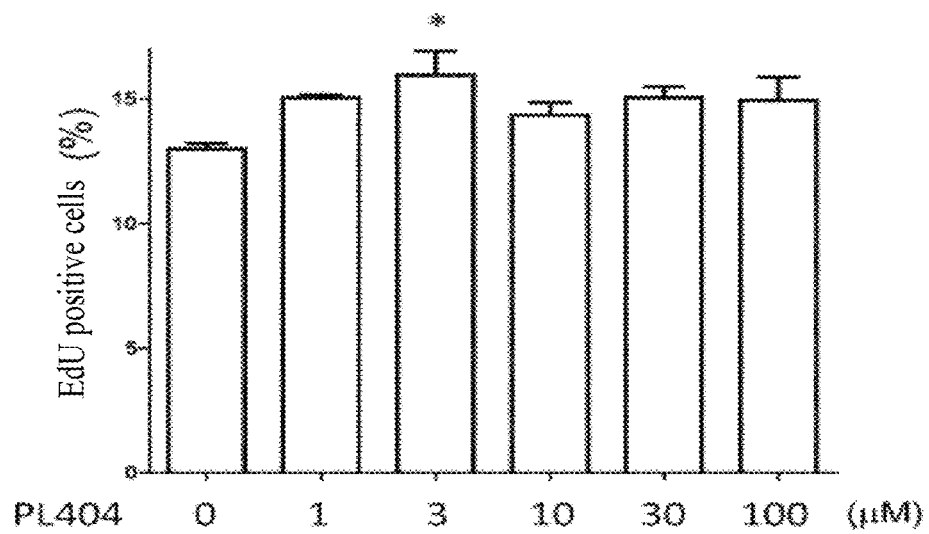
FIG. 5 shows the effect of PL404 on the proliferation of human neural progenitor cells.

The results are shown in FIG. 5. The results show that treatment with PL404 can significantly promote the proliferation of human neural progenitor cells. Compared with the control group not treated with PL404, the level of human neural progenitor cell proliferation is increased by about 30%.

Example 8. Effect of PL405 on the Proliferation of Human Neural Progenitor Cells The method similar to that in Example 7 was used, except that compound PL404 was replaced by PL405, and by detecting the EdU incorporation of human neural progenitor cells, whether PL405 has the effect on promoting proliferation was investigated.

Figure 6:
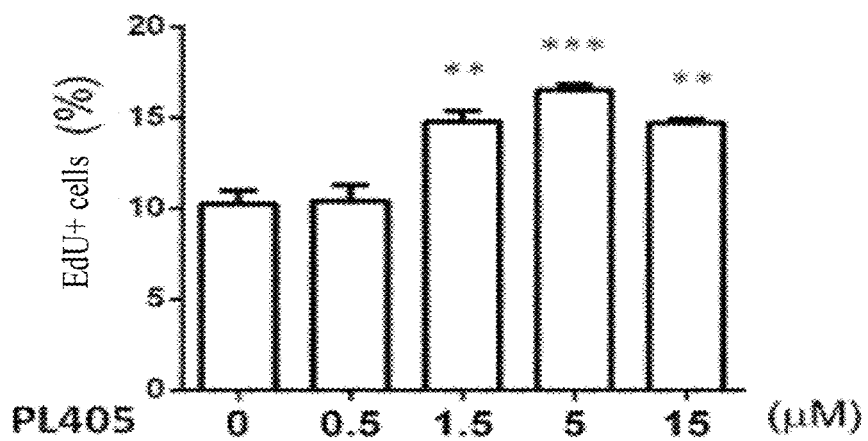
FIG. 6 shows the effect of PL405 on the proliferation of human neural progenitor cells.

The results are shown in FIG. 6. The results show that treatment with PL405 can significantly promote the proliferation of human neural progenitor cells. Compared with the control group, PL405 treatment increases the proliferation level of human neural progenitor cells by about 60%.

All documents mentioned in the present invention are cited as references in this application, as if each document is individually cited as a reference. In addition, it should also be understood that after reading the disclosure of the present invention, various changes or modifications can be made to the present invention by those skilled in the art, and these equivalents also fall within the scope as defined by the appended claims of the present application.

What is claimed is:

1. A compound represented by Formula (I) or a pharmaceutically acceptable salt thereof,

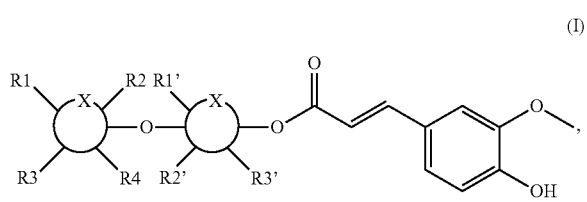

(I)

wherein

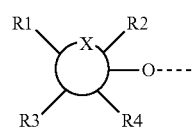

comprises a cyclic structure selected from the group consisting of

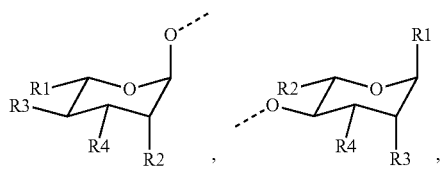

wherein R1-R4 are each independently selected from hydrogen, hydroxyl, C1-C4 alkyl, C2-C4 alkenyl, C2-C4 alkynyl, and halo; or adjacent two groups of R1-R4 are linked to each other to form a five-membered ring with the parent ring, the five-membered ring is a heterocyclic ring containing two O atoms;

and wherein

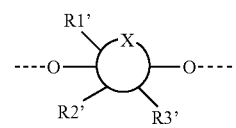

comprises a cyclic structure

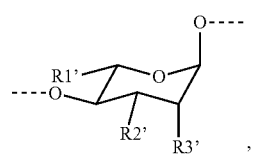

R1'-R3' are each independently selected from hydrogen, hydroxyl, C1-C4 alkyl, C2-C4 alkenyl, C2-C4 alkynyl, and halo.

2. The compound according to claim 1, wherein the compound is

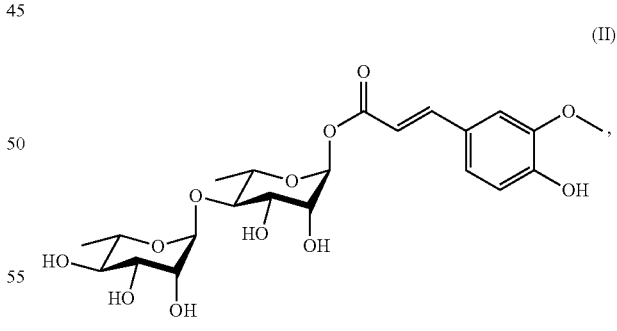

(II)

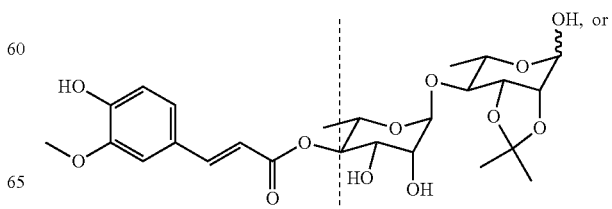

(III)

-continued (IV)

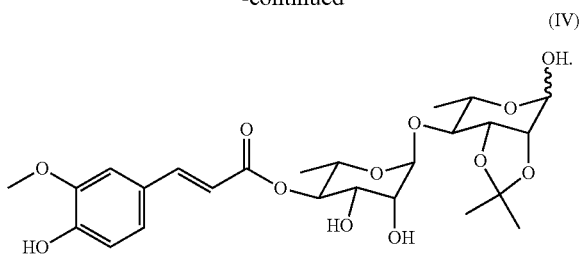

3. A pharmaceutical composition, comprising:
the compound according to claim 1; and
a pharmaceutically acceptable carrier.

4. The pharmaceutical composition according to claim 3, wherein dosage forms of the pharmaceutical composition comprise powder, pulvis, tablets, pills, capsules, sustained release preparations, controlled release preparations, injections, infusions, or suspensions.

5. A pack, comprising the pharmaceutical composition according to claim 3.

6. A method for preparing a compound represented by Formula (II), comprising the step of reacting di-rhamnopyranosylglycoside with tetrabutylammonium fluoride to obtain the compound represented by Formula (II):

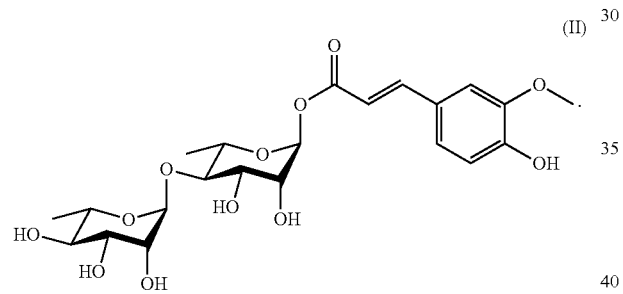

(II)

7. The preparation method according to claim 6, wherein the di-rhamnopyranosylglycoside is obtained by reacting di-rhamnopyranosylthioglycoside with (4-O-tert-butyldimethylsilyl)-ferulic acid.

8. The preparation method according to claim 7, wherein the di-rhamnopyranosylthioglycoside is obtained by reacting rhamnopyranosylthioglycoside with 2,3,4-O-triacetylrhamnosyl-1-O-tricholoracetimidate.

9. A method for preparing a compound represented by Formula (III) or (IV), comprising the step of
reducing the compound

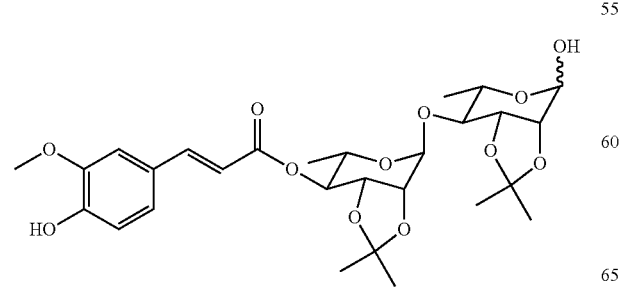

thereby removing the isopropylidene group protecting the vicinal diol to obtain the compound represented by Formula (III) or (IV).

10. The method according to claim 9, wherein the compound

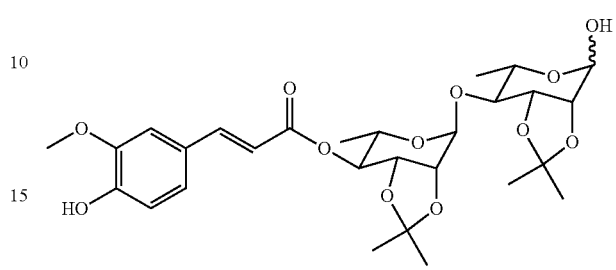

is obtained by the step of condensing the compound

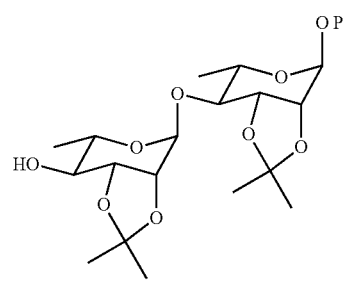

with the compound

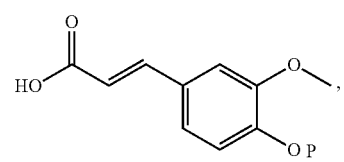

wherein P is H or a protecting group, wherein the protecting group is selected from the group consisting of allyl (All), tert-butoxy carbonyl (Boc), tert-butyldimethylsilyl (TBS), acetate (Ac), benzylamine (Bn), 4-methoxybenzyl ether (PMB), and benzyl carbonate (Cbz).

11. The method according to claim 10, wherein the compound

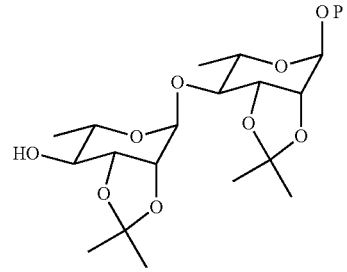

is obtained by the steps of subjecting the compound
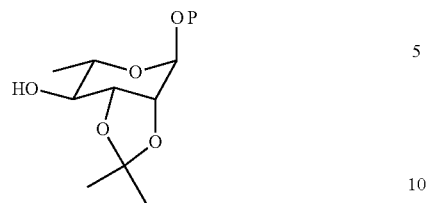
and the compound
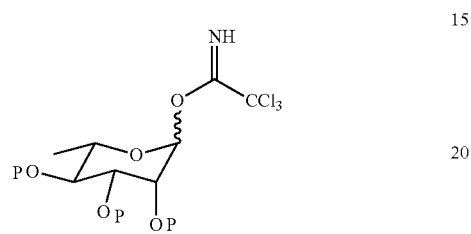
to an addition reaction and protecting the vicinal diol with an isopropylidene group.
* * * * *